United States Patent
Steger et al.

Patent Number: 6,138,500
Date of Patent: Oct. 31, 2000

[54] METHOD AND DEVICE FOR STUDYING THE LIQUID ACCOMMODATING PROPERTIES OF ABSORBENT PRODUCTS

[75] Inventors: Christina Steger, Mölndal; Johan Granat, Göteborg, both of Sweden

[73] Assignee: SCA Hygiene Products AB, Goteborg, Sweden

[21] Appl. No.: 09/343,703

[22] Filed: Jun. 30, 1999

[30] Foreign Application Priority Data

Jul. 6, 1998 [SE] Sweden .................................. 9802430

[51] Int. Cl.$^7$ ...................................................... G01N 5/02
[52] U.S. Cl. .................................................................. 73/73
[58] Field of Search ................................ 73/38, 73, 866, 73/198

[56] References Cited

U.S. PATENT DOCUMENTS

| | | |
|---|---|---|
| 966,078 | 8/1910 | Bowman . |
| 3,952,584 | 4/1976 | Lichstein . |
| 4,357,827 | 11/1982 | McConnell . |
| 5,361,627 | 11/1994 | Levesque . |

FOREIGN PATENT DOCUMENTS 0 333 104 A2  9/1989  European Pat. Off. .

OTHER PUBLICATIONS

The Test Mess–Part IV; James P. Hanson; Nonwovens World Winter 1998; pp. 54–57.

*Primary Examiner*—Robert Raevis
*Attorney, Agent, or Firm*—Burns, Doane, Swecker & Mathis, L.L.P.

[57] ABSTRACT

The invention relates to a method of studying the liquid accommodating property of absorbent products. According to the invention, the amount of liquid received by the absorbent product from a vessel is measured continuously, by measuring the amount of liquid removed from the vessel.

The invention also relates to apparatus for carrying out the method.

10 Claims, 1 Drawing Sheet

FIG. 1
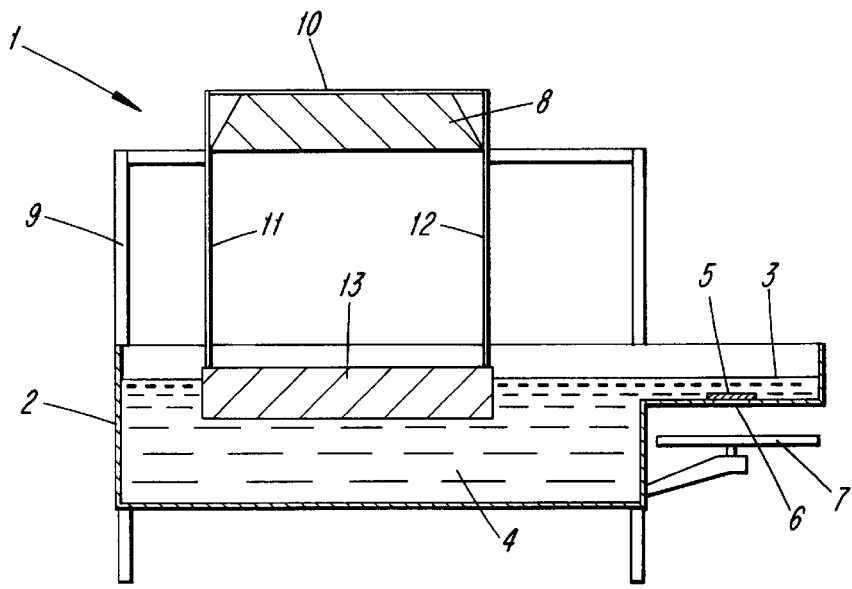
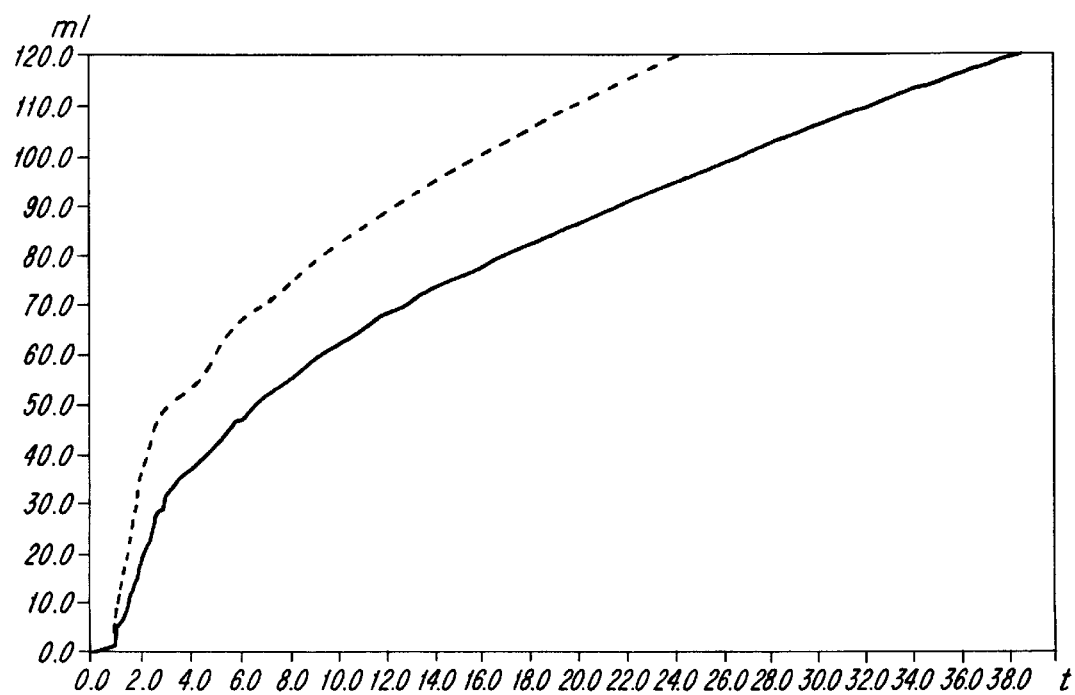
FIG. 2

METHOD AND DEVICE FOR STUDYING THE LIQUID ACCOMMODATING PROPERTIES OF ABSORBENT PRODUCTS

FIELD OF INVENTION

The present invention relates to a method and to a device for studying the liquid accommodating properties of absorbent products.

BACKGROUND OF THE INVENTION

It is not only the total absorption capacity of absorbent products, such as diapers, sanitary napkins and incontinence protectors, that is of interest, in other words the maximum volume of liquid that a product can absorb, but also the ability of the product to transport liquid quickly away from the liquid receiving surface and into the product. The liquid accommodating properties of an absorbent product are normally determined by ascertaining the acquisition time of said product, by which is meant the time taken for a given volume of liquid to penetrate into the product.

A typical method of determining the acquisition time of a product, is to place a pipe or tube on top of the product with the tube orifice pressed thereagainst, and then fill the tube with a determined quantity of liquid. This method is very imprecise in many instances, since the accuracy of the process is influenced by the liquid accommodating properties of the product. The process of liquid accommodation results in the formation of liquid columns of greater or smaller heights, depending on the speed at which the liquid is accommodated, these liquid columns exerting pressure on the product and therewith influencing the result of the measuring process. This makes comparison between the liquid accommodating properties of different products difficult. In order to illustrate the effect of the liquid column, it can be mentioned that the acquisition time in respect of one and the same product has been measured at 8 mm liquid column and 13 mm liquid column and has been found to have a duration of 39 and 26 seconds respectively. The height of the liquid column can thus have a great bearing on the result of the measuring process. This is a serious drawback, since the height of the liquid pillar generated when using this method is dependent on the liquid accommodating properties of the product to be tested. Acquisition times determined in accordance with this method cannot be readily compared with each other and merely provide a rough gauge of the differences in liquid accommodating properties between products.

In "the test mess—part IV", James P. Hanson, NONWOVENS WORLD WINTER 1998, pp 54–57, there is described a method with which the influence of the liquid column is reduced, by providing the measuring tube with a runoff pipe of given height. The amount of liquid delivered can be determined by supplying liquid at a constant rate of flow and measuring the amount of liquid that runs off through said pipe. This enables the acquisition time to be determined. The method also gives an understanding of the volume of liquid received by the product per unit of time, after the liquid in the delivery pipe has reached the runoff level, although it is unable to provide information relating to the liquid accommodation properties of the product prior to this point in time. There is consequently the need of a method that will enable a study to be made of the development of liquid accommodation from the beginning of the process to the point at which an intended volume of liquid has been absorbed. The present invention addresses this need.

SUMMARY OF THE INVENTION

The object of the invention is achieved by means of a method of studying liquid accommodating properties of absorbent products which is characterised in that the volume of liquid received by the absorbent product from a vessel is measured continuously by virtue of measuring the volume of liquid that is taken from the vessel. This method enables the acquisition sequence to be studied in detail.

In one preferred embodiment of the invention, the liquid column is maintained constant above the absorbent product during the measuring process. The liquid column above the absorbent product decreases by at most 1 mm during the measuring process. The measuring process is terminated after the absorbent product has received a specific volume of liquid, and the area of the vessel is made sufficiently large so that the level reduction in the vessel as a result of taking said specific volume of liquid therefrom will be less than 1 mm. The acquisition sequence is thus not influenced by external factors and the method provides a satisfactory result.

The invention also relates to apparatus for studying the liquid accommodating properties of absorbent products, said apparatus being characterised by a vessel that includes a bottom valve which includes an opening; bottom valve manoeuvring means; means for urging an absorbent product against the opening in said bottom valve; and means for measuring the volume of liquid taken from the vessel.

In one preferred embodiment of the invention, that part of the vessel which includes the bottom valve is much shallower than the remainder of the vessel. The means for measuring the volume of liquid that leaves the vessel are comprised of a body which is suspended from measuring scales and which is submerged partially in the liquid in the vessel during a measuring process, said scales measuring the differences in hydrostatic pressure that occur in response to changes in the level of liquid in the vessel.

BRIEF DESCRIPTION OF THE DRAWINGS

The invention will now be described with reference to the accompanying drawings, in which FIG. 1 is a schematic, party cut-away side view of apparatus designed to study the liquid accommodating properties of absorbent products in accordance with one preferred embodiment of the invention; and FIG. 2 shows curves representing the acquisition course followed by two different absorbent products.

DETAILED DESCRIPTION OF ONE EMBODIMENT OF THE INVENTION

The basic concept of the inventive method is to measure the volume of liquid that is taken from a liquid-containing vessel to an absorbent product per unit of time, instead of measuring the time taken for an absorbent product to receive, or accommodate, a given volume of liquid. This enables the entire liquid accommodating process to be studied, as opposed to earlier known methods and the methods described in the introduction, in which solely the acquisition time or the acquisition time plus the final phase of the liquid accommodating process can be measured.

A further principle on which the inventive method is based is one of ensuring that the liquid column above the absorbent product to be tested is not too high and that it is kept generally constant. This is achieved by giving the vessel an area which is so great that the volume of liquid taken from the vessel will give rise solely to a very small reduction in the level of liquid in the vessel. It will be understood that the dimensions of the vessel can be chosen so that this lowering of the liquid level will be as small as is desired.

FIG. 1 is a schematic illusion of one embodiment of apparatus 1 for carrying out the inventive method.

The apparatus 1 includes a vessel 2 that has a shallow part 3 and a deeper part 4. A bottom valve 5 is provided in the shallower part 3. The bottom valve 5 will preferably comprise a slide valve which is manoeuvred so as to fully open or fully close an opening 6 in the shallow part 3 of the vessel 2. Located beneath the opening 6 is an absorbent-product carrying plate 7. The carrier plate can be raised and lowered by means of a suitable mechanism (not shown), such as to enable the upper side of an absorbent product to be brought into abutment with the material surrounding said opening 6.

The apparatus 1 also includes balance scales 8 carried by a stand 9, which also supports the vessel 2. The scales 8 support, in turn, a parallelepipedic body 13 through the medium of a plate 10 and two rods 11, 12. The weight of the body 13 is registered continuously by a register (not shown) included, e.g., in a computer or the like.

The apparatus 1 is used in the following way:

The vessel 2 is first filled with liquid until part of the body 13 is submerged in the liquid and the liquid in the shallow part 3 of the vessel has reached an appropriate level. The bottom valve 5 is, of course, closed while filling the vessel with liquid. The absorbent product whose liquid accommodating properties shall be studied is then placed on the carrier plate 7 and the plate is raised until the upper side of the product comes into tight abutment with the opening 6. In order to eliminate any danger of irregularities in the surface of the absorbent product causing liquid to run off said surface outside the region of the opening 6, the carrier plate 7 is adapted to urge the product against said opening at a given pressure in some suitable way. The carrier plate is preferably provided with a load cell for detecting the pressure with which the carrier plate presses against the bottom of the shallow part 3 of the vessel via the product lying between said plate and said vessel part. This pressure will suitably be 0.01–10 kPa.

The bottom valve 5 is opened when the aforesaid procedure has been completed. The absorbent product then receives liquid from the vessel 2 within the area of the opening 6. The level of liquid in the vessel 2 will fall, as liquid is taken therefrom. This will result in a reduction of the hydrostatic pressure on the body 13, and the weight registered by he scales will increase in proportion with this level difference. With knowledge of the dimensions of the vessel 2 and the body 13 and the density of the liquid present in the vessel, it is easy to calculate the weight increase corresponding to the reduction in liquid volume in the vessel 2. The apparatus 1 includes to this end a calculating unit which continuously recalculates the weight of the liquid volume taken from the vessel and measured by said scales. The calculating unit may conveniently be included in a computer or the like.

When an intended volume of liquid has been removed from the vessel 2, the bottom valve 5 is closed and the carrier plate 7 lowered and the tested absorbent product removed.

A further absorbent product can then be tested, subsequent to filling the vessel 2 with a liquid volume corresponding to the liquid volume received by the absorbent product.

Although not shown, the apparatus 1 illustrated in FIG. 1 includes a control unit, e.g. a computer, which controls the mechanisms the manoeuvre the carrier plate 7 and the bottom valve 5 and which receives and stores the measured values given by the scales and corresponding values of the liquid volume taken from the vessel 2.

Distinct from earlier known methods of measuring acquisition times with the aid of tubes filled with liquid, no build-up of a liquid column above the product to be tested takes place when practicing the inventive method Instead, the height of the liquid column at the start of the measuring process is independent of the product properties and solely dependent on the quantity of liquid contained by the vessel 2. The height of the liquid column decreases as liquid is accommodated, or received, by the product. The reduction in liquid level as a result of the volume of liquid taken from the vessel and by virtue of the liquid accommodation of the absorbent product will be very small, owing to the fact that the vessel 2 is dimensioned so that the volume of liquid in the vessel will be large in relation to the volume of liquid that is then therefrom, and to the fact that the free liquid surface, i.e. the surface area of the vessel minus the surface area of the parallelepipedic body 13 is large in relation to the depth of the vessel. Theoretically, this reduction in liquid level can be made as small as desired, since the vessel can, in theory, be given a surface area of any desired size. In practice, however, the minimum reduction in liquid level is determined by the smallness of those changes in said level that can be registered with sufficient accuracy. As will be apparent from the aforegoing, it is the surface area of the vessel that decides how a small reduction in liquid level can be obtained when taking a given quantity of liquid from the vessel. The depth of the vessel need only be sufficiently large for the liquid column above the opening 6 to be given a desired height or desired heights for the pressure conditions under which the acquisition sequence shall be tested on said products. It is mentioned in this connection, that the height of the body 13 must also be adapted to achieve desired liquid column heights without the level of liquid in the vessel covering the upper side of said body. The pressure reduction on the absorbent product caused by a reduction in the liquid column height of 1 mm or less will have no appreciable influence on the acquisition sequence and the height of the liquid column can therewith be considered to be essentially constant when the vessel is dimensioned so that the level reduction during the measuring process is 1 mm or less in respect of those liquids that are typical when testing the absorption properties of absorbent products, eg 0.9% NaCl.

When using absorbent products of the aforesaid kind, the pressure conditions vary to a large extent. For instance, a relatively large quantity of liquid is discharged simultaneously by the wearer of a diaper, under relatively high pressure. It is therefore of interest to be able to study the course of the acquisition process under different pressure conditions, e.g. under the pressure condition applicable in respect of the aforesaid instantaneous liquid discharge, and under those pressure conditions that apply subsequent to said instantaneous discharge. This can be achieved with the described method, by choosing a desired liquid column height above the absorbent product whose liquid accommodating properties shall be tested. One advantage afforded by the described apparatus is that it can be dimensioned so as to enable different pressure conditions to be tested with one and the same apparatus.

FIG. 2 shows two curves relating to the course followed by the acquisition process in two different diapers, a Bebe Maxi from Carrefour, France, and a Libero® Maxi from SCA Mölnlycke AB, Sweden The curves have been compiled from measurements obtained with an apparatus constructed in the same way as the apparatus 1, with a liquid volume of 5 dm³ and an initial liquid column height of 8 mm in the shallow part of the vessel. The liquid volume taken from the vessel was 120 ml (0.12 dm³) in both instances. The test liquid used was synthetic urine according to the recipe 0.66 g/l magnesium sulphate, 4.47 g/l potassium chloride, 7.60 g/l sodium chloride, 18.00 g/l urea, 3.54 g/l potassium dihydrogen phosphate, 0.745 g/l sodium hydrogen phosphate, 1.00 g/l 0.1%-triton, 0.4 g/l Nykockin/?/ (pigment) and the remainder deionized water. The vessel had a surface area of 26 dm² and the area of the parallelepipedic body was 7.6 dm². The level difference was 0.65 mm.

The fall line curve shows the course followed by the acquisition process for Bebe Maxi, while the broken line curve shows the acquisition course for Libero® Maxi. The acquisition times for 120 ml of synthetic urine were 39 and 24.6 seconds respectively. Both curves are relatively steep at the beginning of the acquisition sequence, meaning that the diapers can initially accommodate a relatively large volume of liquid per unit of time, and then continue, via a curved transition part, in a straight line of constant slope.

The described method thus provides good knowledge of the acquisition sequence of a tested absorbent product. This enables a detailed study to be made of how changes in the product influence the acquisition sequence, both quantitatively and qualitatively, which is not possible with the earlier known methods. Naturally, different layers or different combinations of layers present in an absorbent product can be studied. The method also enables fabricated large discharge volumes to be studied, and the studies can be carried out under all pressure conditions that can occur with products of the aforedescribed kind.

It will be understood that the described and illustrated embodiment can be varied within the scope of the invention, particularly with respect to the shape and size of the vessel. Furthermore, other methods can be used to measure the level changes, e.g. with the aid of laser or ultrasonics, provided that efficiently small level variations can be measured. Other types of bottom valves than slide valves may be used, of course. It is also conceivable to use a variable bottom opening in the shallow part of the vessel, so as to enable the apparatus to be used for products of different sizes. Bodies that have a shape other than parallelepipedic may, of course, be used in the apparatus, although the side surfaces of such bodies will preferably be vertical so as to facilitate calculation of the level reduction during the measuring process. The invention is therefore solely restricted by the contents of the following claims.

What is claimed is:

1. A method of studying the liquid accommodating properties of an absorbent article comprising the steps of:

placing an absorbent article under an opening in a bottom portion of a vessel filled with liquid;

allowing the liquid to exit the vessel onto the absorbent article from the opening; and measuring the volume of liquid received by the absorbent article from the vessel, by measuring the volume of liquid removed from the vessel.

2. The method claimed in claim 1, further comprising urging the absorbent article against the opening.

3. The method claimed in claim 1, wherein the volume of liquid is measured continuously.

4. A method according to claim 1, wherein keeping the liquid column above the absorbent product essentially constant during the measuring process.

5. A method according to claim 4, wherein by reducing the liquid column above the absorbent product by not more than 1 mm during the measuring process.

6. A method according to claim 1, wherein terminating the measuring process subsequent to the absorbent product having received a given amount of liquid; and by making the area of the vessel so large that the reduction in liquid level in the vessel as a result of taking said specific volume of liquid from said vessel will be less than 1 mm.

7. A method according to claim 1, wherein continuously measuring the reduction in liquid level in the vessel.

8. Apparatus for studying the liquid accommodating properties of absorbent products, wherein a vessel which includes a bottom valve having an opening; bottom valve manoeuvring means; means for urging an absorbent product against the bottom valve opening; and means for measuring the amount of liquid that leaves the vessel.

9. Apparatus according to claim 8 wherein a part of the vessel which includes the bottom valve is significantly shallower than the remainder of the vessel.

10. Apparatus according to claim 9, wherein the means for measuring the amount of liquid that leaves the vessel comprises a body which is suspended from scales and which is partially submerged in the liquid in said vessel during a measuring process, wherewith the scales measure the differences in hydrostatic pressure that occur with changes in the liquid level in said vessel.

\* \* \* \* \*